(12) United States Patent
Goshen et al.

(10) Patent No.: US 11,417,034 B2
(45) Date of Patent: Aug. 16, 2022

(54) SPECTRAL IMAGING WITH A NON-SPECTRAL IMAGING SYSTEM

(71) Applicant: KONINKLIJKE PHILIPS N.V., Eindhoven (NL)

(72) Inventors: Liran Goshen, Pardes-Hanna (IL); Mordechay Pinchas Freiman, Zichron-Yaakov (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 207 days.

(21) Appl. No.: 16/962,261

(22) PCT Filed: Jan. 7, 2019

(86) PCT No.: PCT/EP2019/050197
§ 371 (c)(1),
(2) Date: Jul. 15, 2020

(87) PCT Pub. No.: WO2019/141527
PCT Pub. Date: Jul. 25, 2019

(65) Prior Publication Data
US 2021/0065410 A1     Mar. 4, 2021

Related U.S. Application Data

(60) Provisional application No. 62/617,774, filed on Jan. 16, 2018.

(51) Int. Cl.
*A61B 6/00*     (2006.01)
*G06T 11/00*    (2006.01)
(Continued)

(52) U.S. Cl.
CPC ............ *G06T 11/005* (2013.01); *A61B 6/032* (2013.01); *A61B 6/5205* (2013.01); *G06N 3/08* (2013.01);
(Continued)

(58) Field of Classification Search
CPC ...................................................... A61B 6/482
See application file for complete search history.

(56) References Cited

U.S. PATENT DOCUMENTS 8,938,110 B2    1/2015  Goshen
10,282,820 B2   5/2019  Goshen
(Continued)

FOREIGN PATENT DOCUMENTS

WO   WO2016063170 A1   4/2016

OTHER PUBLICATIONS

PCT International Search Report, International Application No. PCT/EP2019/050197, dated May 8, 2019.
(Continued)

*Primary Examiner* — Dani Fox
(74) *Attorney, Agent, or Firm* — Larry Liberchuk (57) ABSTRACT

An imaging system (102) includes a radiation source (112) configured to emit X-ray radiation, a detector array (114) configured to detect X-ray radiation and generate a signal indicative thereof, an a reconstructor (116) configured to reconstruct the signal and generate non-spectral image data. The imaging system further includes a processor (124) configured to process the non-spectral image data using a deep learning regression algorithm to estimate spectral data from a group consisting of spectral basis components and a spectral image.

20 Claims, 7 Drawing Sheets

(51) Int. Cl.
G16H 30/40 (2018.01)
A61B 6/03 (2006.01)
G06N 3/08 (2006.01)

(52) U.S. Cl.
CPC ............ *G16H 30/40* (2018.01); *A61B 6/481* (2013.01); *A61B 6/483* (2013.01); *G06T 2210/41* (2013.01)

(56) References Cited

U.S. PATENT DOCUMENTS

| | | | |
|---|---|---|---|
| 2012/0224760 A1 | 9/2012 | Goshen | |
| 2014/0133729 A1 | 5/2014 | Goshen | |
| 2015/0371378 A1* | 12/2015 | Schmidt | G06K 9/6265 382/131 |
| 2016/0209995 A1 | 7/2016 | Jeon | |
| 2016/0307330 A1 | 10/2016 | Goshen | |
| 2017/0337713 A1 | 11/2017 | Hoelzer | |

OTHER PUBLICATIONS

Sui Li et al., "Pseudo Dual Energy CT Imaging Using Deep Learning Based Framework: Initial Study", arxiv.0rg, Cornell University Library, 201 0lin Library Cornell University Ithaca, NY 14853, Nov. 20, 2017.

Xu S. et al., "Deep Residual Learning in CT Physics: Scatter Correction for Spectral CT", 2017 IEEE Nuclear Science Symposium and Medical Imaging Conference (NSS/MIC), Oct. 2017.

Alvarez et al., "Energy Selective Reconstructions in X-Ray Computerized Tomography", Physics in Medicine and Biology, vol. 21, No. 5, pp. 733-744, Sep. 1976.

Carmi R. et al., "A Unique Noncathartic CT CoIonography Approach by Using Two-Layer Dual-Energy MDCT and a Special Algorithmic Colon Cleansing Method." 2008 IEEE Nuclear Science Symposium Conference Record, Oct. 2008. NSS'08. IEEE. IEEE, 2008.

Gohen L. et al., "An Iodine-Calcium Separation Analysis and Virtually Non-Contrasted Image Generation Obtained with Single Source Dual Energy MDCT", In IEEE Nucl Sci Symp Conf Rec , pp. 3868-3870, Oct. 2008.

Goodfellow I.J. et al., "Generative Adversarial Nets", Advances in Neural Information Processing Systems, pp. 2672-2680, Jun. 10, 2014.

Heismann B. J. et al., "Density and Atomic Number Measurements with Spectral X-Ray Attenuation Method", Journal of Applied Physics, vol. 94, issue 3, Aug. 2003.

Long J. et al., "Fully Convolutional Networks for Semantic Segmentation." Proceedings of the IEEE Conference on Computer Vision and Pattern Recognition (CVPR), 2015, pp. 3431-3440.

Ronneberger O. et al., "U-Net: Convolutional Networks for Biomedical Image Segmentation", Medical Image Computing and Computer-Assisted Intervention (MICCAI), Springer, LNCS, vol. 9351: 234-241, 2015.

Gouk H.G.R. et al., "Fast Sliding Window Classification with Convolutional Neural Networks," IVNVZ '14 Proceedings of the 29th International Conference on Image and Vision Computing New Zealand, pp. 114-118, Nov. 19-21, 2014.

Joshi M. et al., "Effective Atomic Number Accuracy for Kidney Stone Characterization Using Spectral CT", Proceedings of SPIE—The International Society for Optical Engineering, vol. 7622, Mar. 2010.

Johnson T.R.C. et al., "Medical Radiology/Diagnostic Imaging: Dual Energy CT in Clinical Practice", Springer, 2011, last section of Part I—pp. 43-54; part II Vascular System, pp. 55-82.

* cited by examiner

SPECTRAL IMAGING WITH A NON-SPECTRAL IMAGING SYSTEM

FIELD OF THE INVENTION

The following generally relates to imaging and more particularly to estimating spectral images from non-spectral images produced by a non-spectral imaging system, and is described with particular application to computed tomography (CT), but is also amenable to other non-spectral imaging systems.

BACKGROUND OF THE INVENTION

A traditional computed tomography (CT) scanner generally includes an x-ray tube mounted on a rotatable gantry opposite a detector array including one or more rows of detector pixels. The x-ray tube rotates around an examination region located between the x-ray tube and the detector array, and emits polychromatic radiation that traverses the examination region and an object or subject disposed therein. The detector array detects radiation that traverses the examination region and generates projection data indicative of the examination region and the object or subject disposed therein.

A reconstructor processes the projection data and generates volumetric image data indicative of the examination region and the object or subject disposed therein. The volumetric image data can be processed to generate one or more images that include the scanned portion of the object or subject. The resulting image(s) includes pixels that typically are represented in terms of gray scale values corresponding to relative radiodensity. Such information reflects the attenuation characteristics of the scanned subject and/or object, and generally shows structure such as anatomical structures within a patient, physical structures within an inanimate object, and the like.

The detected radiation also includes spectral information as the absorption of the radiation by the subject and/or object is dependent on the energy of the photons traversing therethrough. Such spectral information can provide additional information such as information indicative of the elemental or material composition (e.g., atomic number) of the tissue and/or material of the subject and/or object. However, with such a scanner the projection data does not reflect the spectral characteristics as the signal output by the detector array is proportional to the energy fluence integrated over the energy spectrum. As utilized herein, a scanner of this configuration is referred to herein as a non-spectral scanner.

A computed tomography scanner configured for spectral imaging (a spectral scanner) leverage this spectral information to provide further information indicative of elemental or material composition. One approach includes using multiple X-ray tubes, each emitting an X-ray beam having a different energy spectrum. Another approach includes fast kVp switching in which the voltage across the tube is switched between different voltages such that measurements at multiple energies are taken. Another approach includes a multi-layer indirect conversion detector with an uppermost layer that detects lower energy X-rays and a bottommost layer that detects higher energy X-ray. Another approach uses direct conversion photon detectors which energy bins photons in multiple energy ranges.

A dual-energy scanner is a specific configuration that utilizes two attenuation values acquired concurrently at two photon energies to solve for photoelectric effect and Compton scattering basis components. Because any two linearly independent sums of two basis functions span the entire attenuation coefficient space, any material can be represented by a linear combination of two basis materials. The basis material components can be used to produce, e.g., a non-spectral image and/or a spectral image such as an image for an energy band, a virtual monochromatic image, a contrast agent quantitative map, a virtual non-contrast image, a material cancellation image, an effective atomic number image, an electron density image, and/or other spectral image.

Unfortunately, the specialized acquisition hardware of such a system, i.e. multiple X-ray tubes, kVp switching hardware and circuitry, and/or spectral detectors (indirect conversion multi-layer or direct conversion), can be expensive and increases overall scanner cost. In addition, scanners configured for spectral imaging generally cannot utilize existing acquisition protocols, reconstruction settings and/or dataflow and storage configuration of non-spectral scanners, and thus, may require adapting the acquisition protocols, reconstruction settings and/or dataflow and storage configuration. As a consequence, image quality may be degraded (e.g., temporal resolution may be reduced), the ability to produce non-spectral images may be lost, and/or data storage capacity may have to be significantly increased.

SUMMARY OF THE INVENTION

Aspects described herein address the above-referenced problems and others.

In one aspect, an imaging system includes a radiation source configured to emit X-ray radiation, a detector array configured to detect X-ray radiation and generate a signal indicative thereof, an a reconstructor configured to reconstruct the signal and generate non-spectral image data. The imaging system further includes a processor configured to process the non-spectral image data using a deep learning regression algorithm to estimate spectral data from a group consisting of spectral basis components and a spectral image.

In one aspect, an imaging system includes a radiation source configured to emit X-ray radiation, a detector array configured to detect X-ray radiation and generate a signal indicative thereof, an a reconstructor configured to reconstruct the signal and generate non-spectral image data. The imaging system further includes a processor configured to train a deep learning regression algorithm to estimate spectral data from the non-spectral image data using a hybrid training algorithm.

In another aspect, a computer readable storage medium is encoded with computer readable instructions, which, when executed by a computer processor of a computing system, causes the computer processor to: emit X-ray radiation with a radiation source, detect emitted X-ray radiation with a detector array and generate a signal indicative thereof, reconstruct the signal and generate non-spectral image data, and process the non-spectral image data using a deep learning regression algorithm to estimate spectral data from a group consisting of spectral basis components and a spectral image.

Those skilled in the art will recognize still other aspects of the present application upon reading and understanding the attached description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

FIG. 1 schematically illustrates an example system including a spectral results module.

DETAILED DESCRIPTION OF EMBODIMENTS

Figure 1:
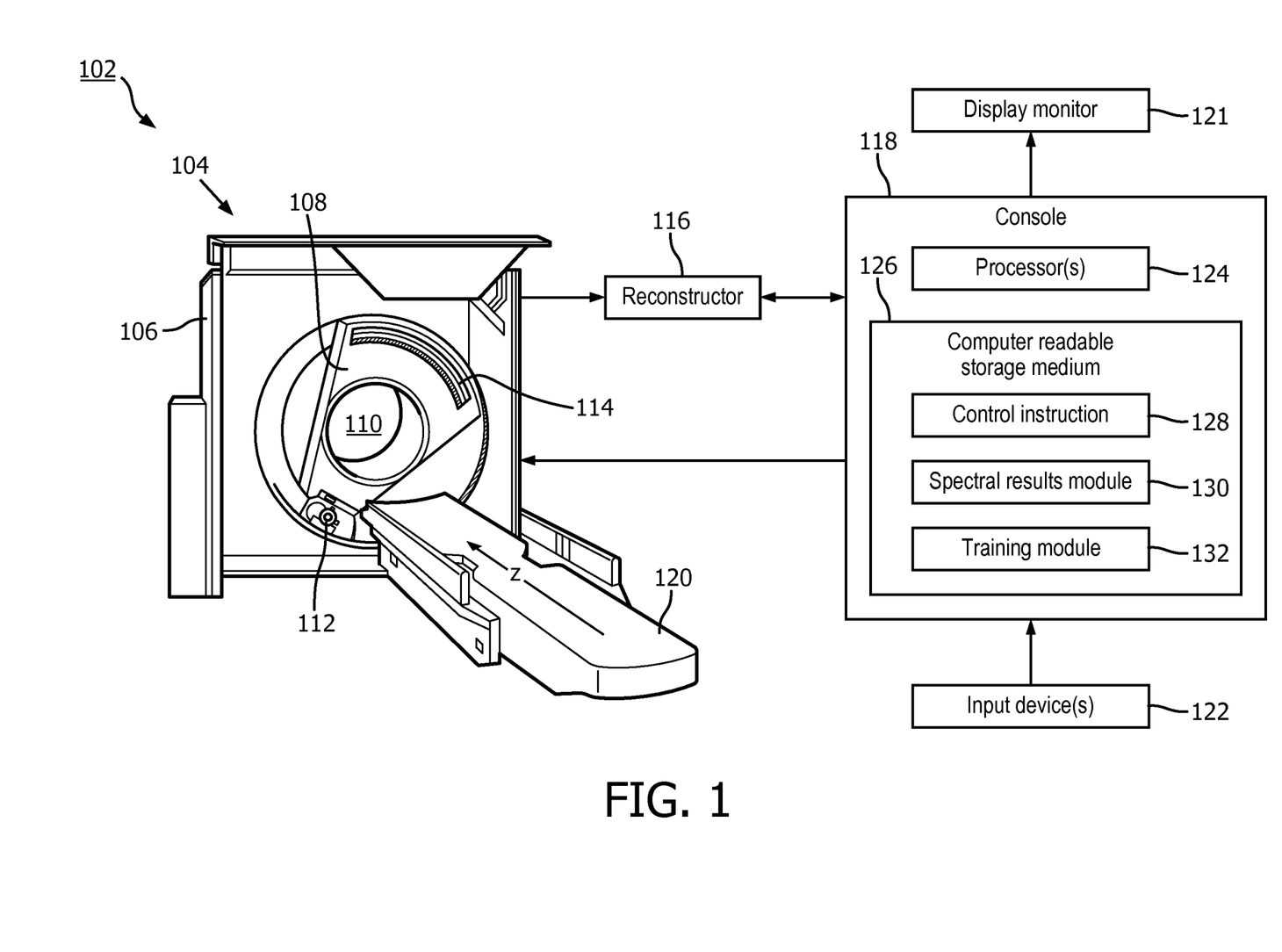

FIG. 1 schematically illustrates a system 102 including an imaging system 104, such as a non-spectral CT scanner (i.e., a CT scanner not configured for spectral imaging). The imaging system 104 includes a generally stationary gantry 106 and a rotating gantry 108, which is rotatably supported by the stationary gantry 106 and rotates around an examination region 110 about a z-axis. A radiation source 112, such as an x-ray tube, is rotatably supported by the rotating gantry 108, rotates with the rotating gantry 108, and emits radiation that traverses the examination region 110.

A radiation sensitive detector array 114 subtends an angular arc opposite the radiation source 112 across the examination region 110. The illustrated radiation sensitive detector array 114 includes one or more rows of layer indirect conversion detector elements (e.g., scintillator/photosenser). The array 114 detects radiation traversing the examination region 110 and generates projection data (line integrals) indicative thereof. A reconstructor 116 reconstructs the projection data, generating non-spectral volumetric image data indicative of the examination region 110. A subject support 120, such as a couch, supports an object or subject in the examination region 110.

An operator console 118 includes a computer with a human readable output device such as a display monitor 121 and an input device 122 such as a keyboard, mouse, etc. The console 118 further includes a processor 124 (e.g., a central processing unit (CPU), a microprocessor, etc.) and computer readable storage medium 126 (which excludes transitory medium) such as physical memory, a memory device, and/or other non-transitory storage medium. The processor 124 is configured to execute a control instruction 128, which allows an operator to control an operation such as select an acquisition, reconstruction, etc. protocol, set an acquisition, reconstruction, etc. parameter, start a scan, select a mode of operation, etc.

The one or more processors 124 are also configured to execute instructions of a spectral results module 130 and a training module 132. The spectral results module 130 is configured to process the non-spectral volumetric image data along with acquisition and reconstruction parameters and estimate spectral data such as basis components (e.g., photoelectric electric and Compton scattering, etc.) and/or spectral images (e.g., virtual monochromatic, iodine map, etc.). As described in greater detail below, in one instance, estimating the spectral data includes employing a deep learning regression algorithm trained with the training module 132. The training module 132 is executed in a training mode, and the spectral results module 130 is operated in an operation mode.

With the configuration described herein, the non-spectral imaging system 102 reconstructs non-spectral volumetric image data and estimates spectral data therefrom. As such, the non-spectral imaging system 102 does not require specialized acquisition hardware (e.g., multiple X-ray tubes, kVp switching hardware and circuitry, and/or spectral detectors) to produce spectral volumetric image data. This mitigates an increase in overall system cost associated with such specialized hardware. Furthermore, the non-spectral imaging system 102 can utilize acquisition and/or reconstruction protocols and/or dataflow and storage configuration of non-spectral scanners, which mitigates degradation of image quality and/or increased data storage capacity relative to a configuration which requires adaption thereof.

Figure 2:
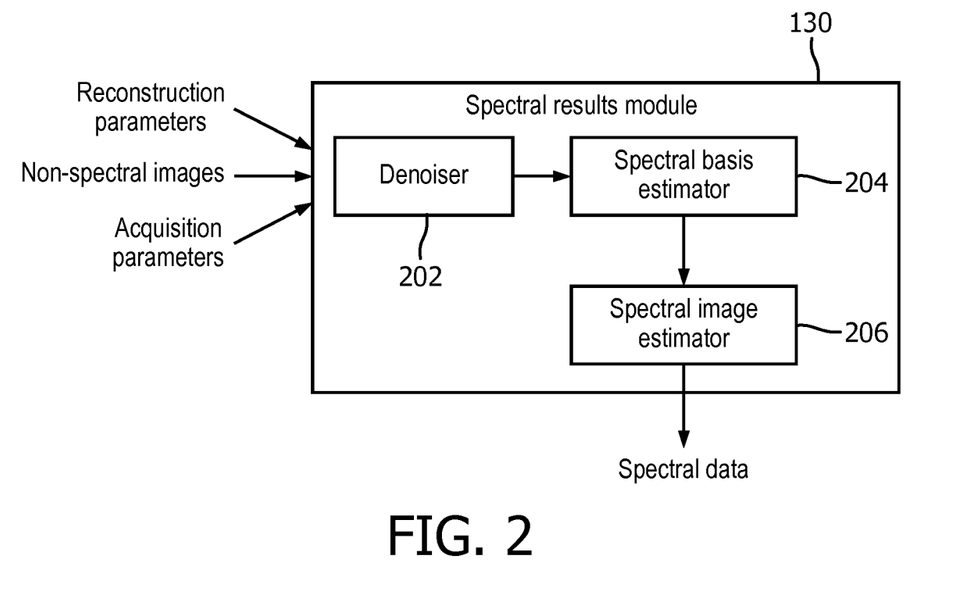
FIG. 2 schematically illustrates an example of the spectral results module with a denoiser, a spectral basis estimator and a spectral image estimator.

FIG. 2 schematically illustrates an example of the spectral results module 130.

In this example, the spectral results module 130 receives the non-spectral images, the acquisition protocol parameters, and the reconstruction protocol parameters as input. Examples of acquisition protocol parameters include scan type, body part, mA (X-ray tube current in milliamperes), mAs (X-ray intensity as the product of mA and exposure time in seconds), kVp (X-ray tube peak kilovoltage), rotating source 108 rotation time, X-ray beam collimation, pitch or subject support 120 speed per rotation, and/or other acquisition protocol parameter(s). Examples of reconstruction protocol parameters include reconstruction filter, reconstruction algorithm, slice thickness, slice increment, matrix size, field of view, and/or other reconstruction protocol parameter(s). The spectral results module 130 outputs spectral data (i.e. spectral basis components and/or spectral images).

A denoiser 202 removes noise from the input non-spectral images using a noise removal algorithm. An example algorithm is described in patent application US 2012/0224760 A1, filed Oct. 29, 2010, and entitle "Enhanced Image Data/Dose Reduction," which is incorporated by reference herein in its entirety. In one instance, this improves contrast to noise ratio (CNR) of the input images. Additionally, or alternatively, this could improve the performance of the system 102. A spectral basis estimator 204 processes the denoised non-spectral images and estimates, based on the input acquisition and reconstruction protocol parameters, spectral basis components. In this example, the spectral basis estimator 204 estimates photoelectric effect and Compton scattering basis components.

A spectral image estimator 206 processes the estimated basis components and predicts spectral images. An example algorithm is described in patent application US20140133729A1. "Image processing for spectral CT,"

which is incorporated by reference herein in its entirety. Other suitable algorithms include Goshen, et al., "An iodine-calcium separation analysis and virtually non-contrasted image generation obtained with single source dual energy MDCT, "In IEEE Nucl Sci Symp Conf Rec, (2008, October), pp. 3868-3870, Heismann et al., "Density and atomic number measurements with spectral x-ray attenuation method," Journal of applied physics 94.3 (2003): 2073-2079, and Joshi et al., "Effective atomic number accuracy for kidney stone characterization using spectral CT," Proc SPIE. Vol. 7622, 2010.

Figure 3:
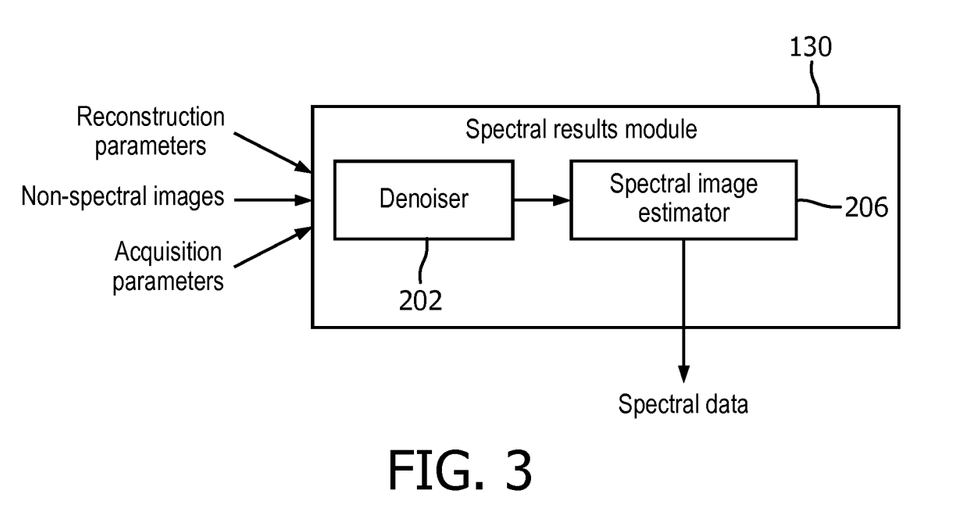
FIG. 3 schematically illustrates an example of the spectral results module with the denoiser and the spectral image estimator.

FIG. 3 schematically illustrates a variation of the spectral results module 130 of FIG. 2 in which the spectral basis estimator 204 is omitted. In this configuration, the spectral image estimator 206 estimates the spectral basis components and/or the spectral images directly from the denoised non-spectral images. The spectral results module 130 outputs the spectral data (i.e. spectral basis components and/or spectral images).

Figure 4:
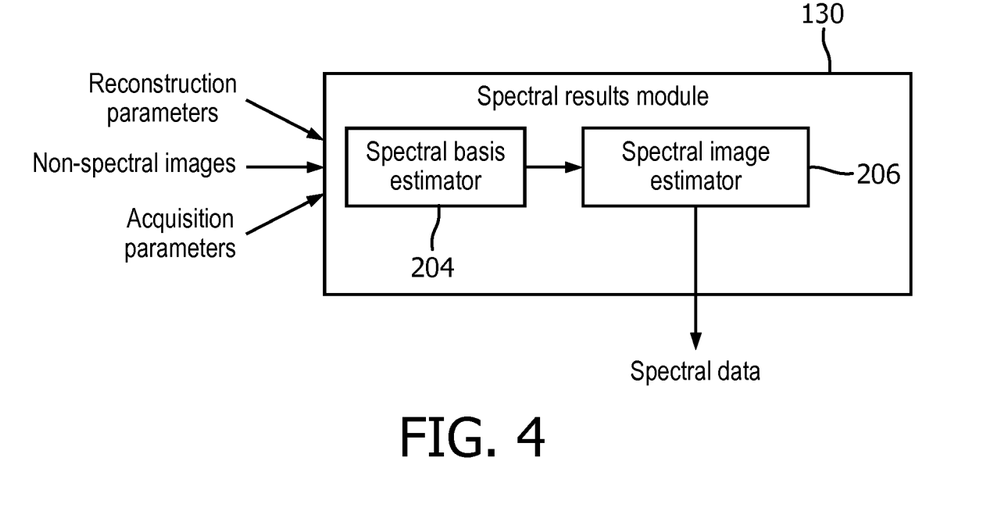
FIG. 4 schematically illustrates an example of the spectral results module with the spectral basis estimator and the spectral image estimator.

FIG. 4 schematically illustrates another variation of the spectral results module 130 of FIG. 2 in which the denoiser 202 is omitted. In this configuration, the spectral basis estimator 204 estimates the basis components directly from the input non-spectral images (i.e., no denoising), and the spectral image estimator 206 produces spectral data therefrom. The spectral results module 130 outputs the spectral data (i.e. spectral basis components and/or spectral images).

Figure 5:
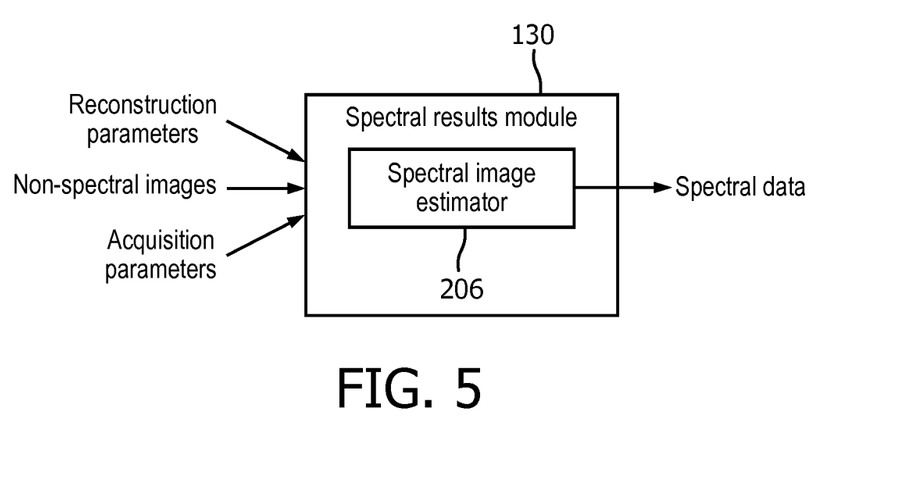
FIG. 5 schematically illustrates an example of the spectral results module with the spectral image estimator.

FIG. 5 schematically illustrates another variation of the spectral results module 130 of FIG. 2 in which the denoiser 202 and the spectral basis estimator 204 are omitted. In this configuration, the spectral image estimator 206 estimates the spectral basis components and/or the spectral images directly from the input non-spectral images (i.e., no denoising). The spectral results module 130 outputs the spectral data (i.e. spectral basis components and/or spectral images).

Figure 6:
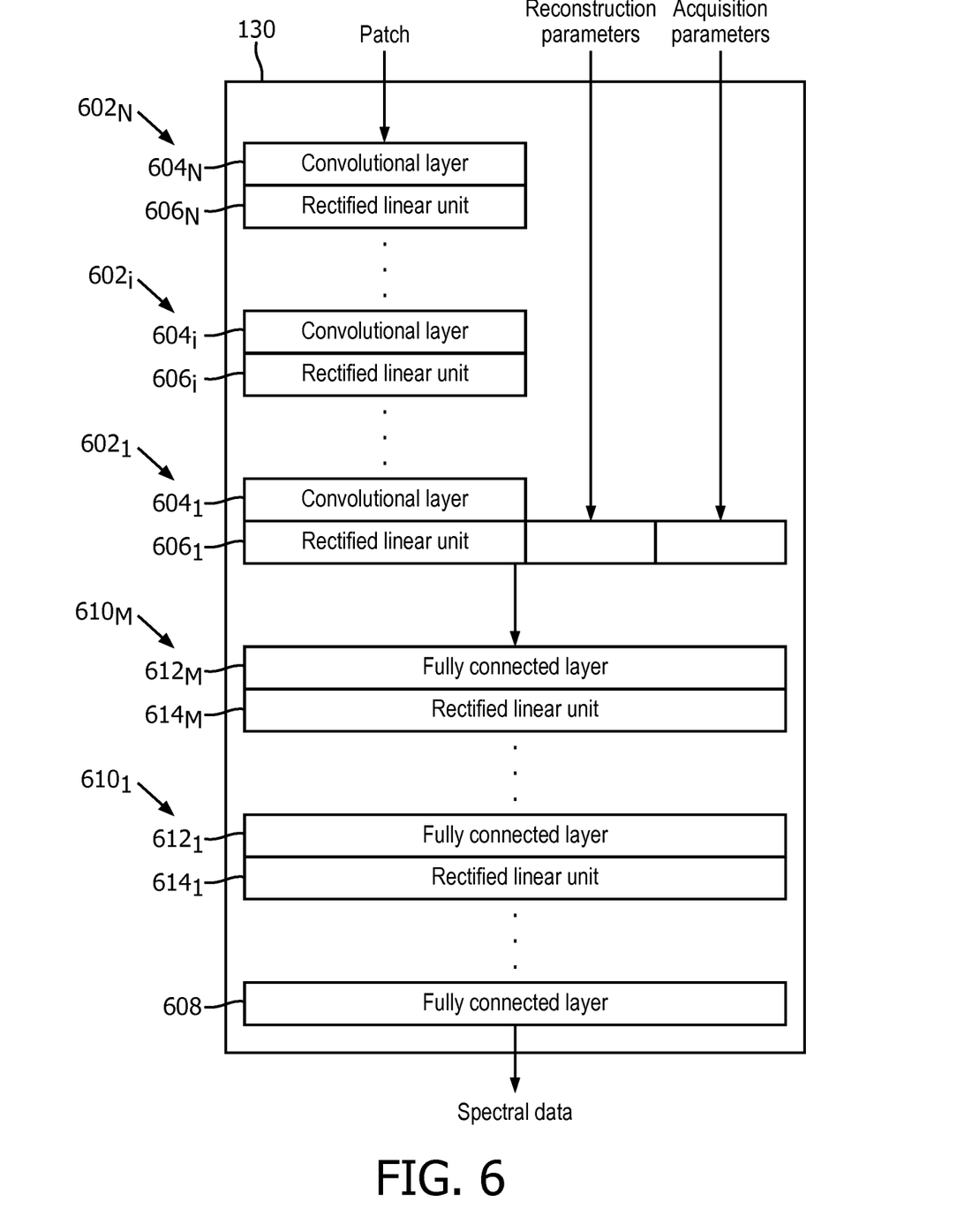
FIG. 6 schematically illustrates an example of the spectral basis estimator and/or the spectral image estimator.
Figure 7:
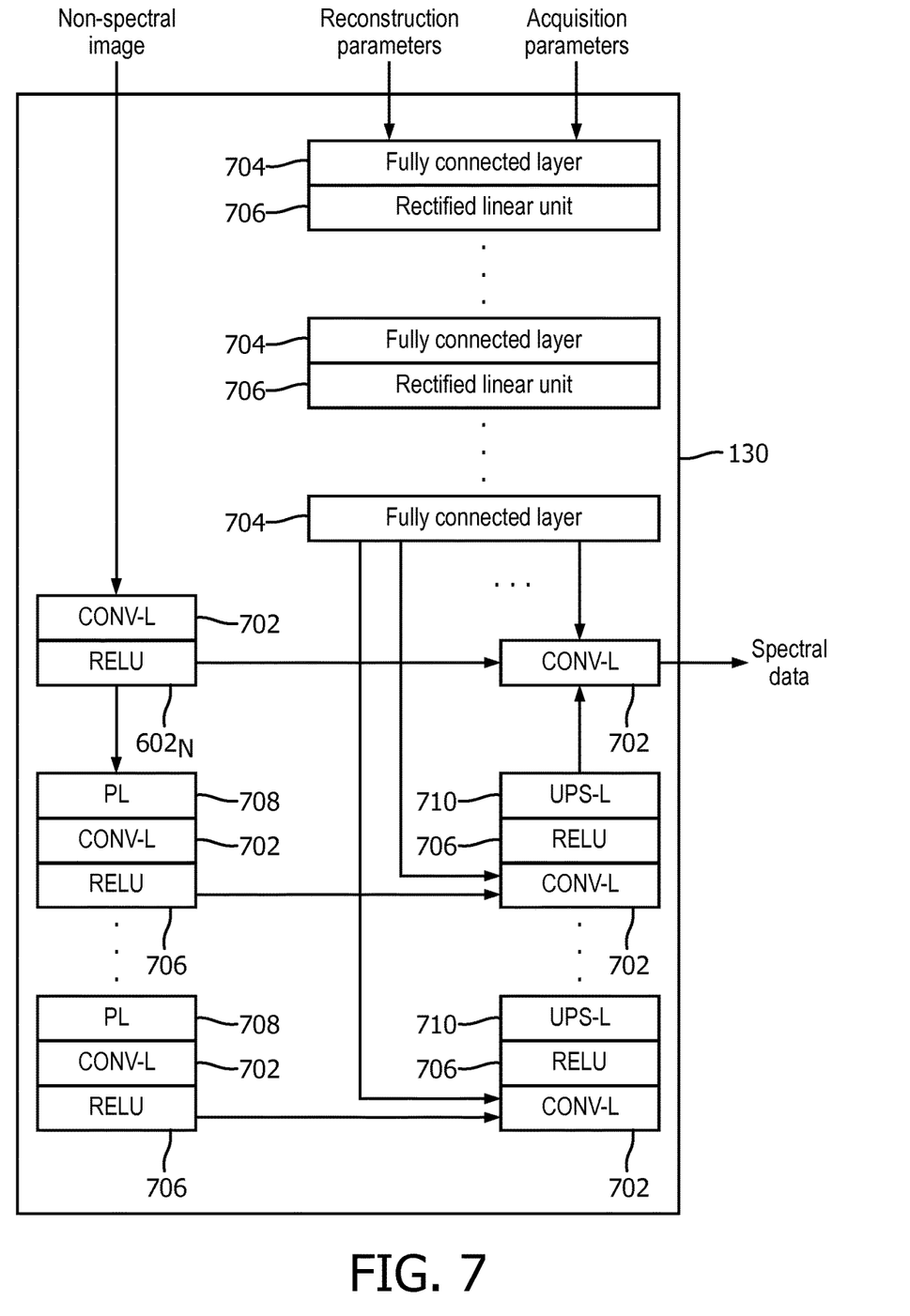
FIG. 7 schematically illustrates another example of the spectral basis estimator and/or the spectral image estimator.

FIGS. 6 and 7 schematically illustrate examples of the deep learning algorithm. In these examples, the deep learning algorithm includes a feed-forward artificial neural network such as a convolutional neural network and/or other neural network that analyzes visual imagery. In another example, the spectral data estimator 204 employs another algorithm.

Initially referring to FIG. 6, a sliding-window algorithm is utilized, which estimates the spectral image voxel-by-voxel.

The algorithm receives, as input, a patch of voxels, which includes a voxel value of the non-spectral image at a location (x,y,z) to be estimated in the spectral data and a local-volume (e.g., 3×3×3, 5×5×5, 7×7×7, etc.) of voxel values around that voxel value. The algorithm includes N (where N is an integer equal or greater than one) pairs of convolutional layers/rectified linear units, including a first pair $602_1$ with a convolutional layer $604_1$ and a rectified linear unit $606_1$, . . . , an ith pair $602_i$ with a convolutional layer $604_i$ and a rectified linear unit $606_i$ . . . , and an Nth pair $602_N$ with a convolutional layer $604_N$ and a rectified linear unit $606_N$.

Each of the convolutional layers $604_1$, . . . , $604_i$, . . . , $604_N$ (also referred to collectively herein as convolutional layers 604) includes convolutional neurons that apply a convolution operation to the input. In one instance, this includes convolving a set of kernels across a width and a height of the input volume, computing a dot product between the entries of the filter and the input volume. Each of the rectified linear units $606_1$, . . . , $606_i$, . . . , $606_N$ (also referred to collectively herein as rectified linear units 606) applies a non-linear activation function to its input, which increases nonlinear properties of the overall network. Example of suitable functions include, but are not limited to, max(0,x), tanh(x), and $(1+e^{-x})^{-1}$.

The algorithm further includes a fully connected layer 608 and M (where M is an integer equal or greater than zero) pairs of fully connected layers/rectified linear units, including a first pair $610_1$ with a fully connected layer $612_1$ and a rectified linear unit $614_1$, . . . , and an Mth pair $612M$ with a fully connected layer $612M$ and a rectified linear unit $614_M$. The fully connected layer (layer $612M$ in the illustrated example) after the last pair of convolutional layers/rectified linear units (pair $602_1$ in the illustrated example) receives, as input, the output of that last pair rectified linear units $606_1$, with the acquisition and reconstruction parameters added thereto.

Each of the fully connected layers $612_1$, . . . , and $612M$ (also referred to collectively herein as fully connected layers 612) combines all of the features learned by the previous layers across the image to identify patterns. Each of the rectified linear units $614_1$, . . . , and $614M$ (also referred to collectively herein as convolutional layers 614) are configured similar to the rectified linear units 606 and applies a non-linear activation function to its input. The final fully connected layer (the fully connected layer 608) combines all the learned features to estimate the spectral voxel value at the location (x,y,z) in the spectral basis component and/or spectral image being estimated.

Turning to FIG. 7, a fully convolution regression network algorithm is utilized, which concurrently estimates groups of voxels, including an entire image.

The algorithm includes at least two convolutional layers 702 (also referred to as conv-l), at least one fully connected layer 704, and at least one rectified linear unit 706 (also referred to as relu). Convolutional layers, fully connected layers, and/or the rectified linear units are configured to perform the same functions as those described in connection with the embodiment of FIG. 6 and thus are not described again here. The algorithm further includes at least one pooling layer (PL) 708 and at least one up-sampling layer (ups-l) 710.

The at least one pooling layer 708 down-samples its input, e.g., using a non-linear down-sampling algorithm. In the illustrated example, the at least one pooling layer 708 employs a max pooling function, which partitions the input into a set of non-overlapping rectangles and, for each such sub-region, outputs the maximum, reducing the spatial size of the input. Other suitable algorithms include average pooling or L2-norm pooling. The at least one up-sampling layer 710 up-samples its input, e.g., back to the original size of the input or other predetermined size.

Examples of a sliding-window and/or a fully convolution regression network are further described in Gouk, et al., "Fast Sliding Window Classification with Convolutional Neural Networks," IVNVZ '14 Proceedings of the 29th International Conference on Image and Vision Computing New Zealand, Pages 114-118, Nov. 19-21, 2014, "Fully convolutional networks for semantic segmentation," Proceedings of the IEEE Conference on Computer Vision and Pattern Recognition, 2015, and Ronneberger, et al., "U-Net: Convolution Networks for Biomedical Image Segmentation," Medical Image Computing and Computer-Assisted Intervention (MICCAI), Springer, LNCS, Vol. 9351: 234-241, 2015.

Figure 8:
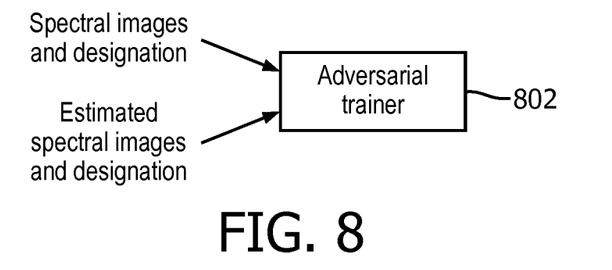
FIG. 8 schematically illustrates training of an adversarial trainer.
Figure 9:
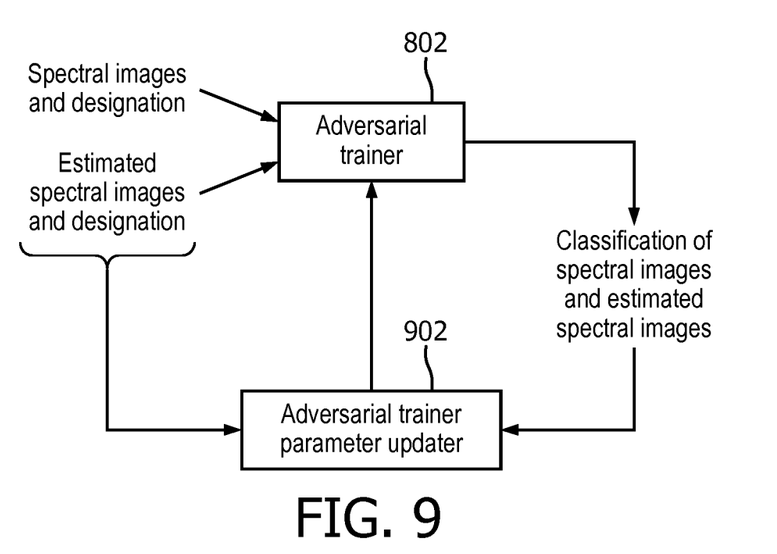
FIG. 9 schematically illustrates further training for the adversarial trainer.
Figure 10:
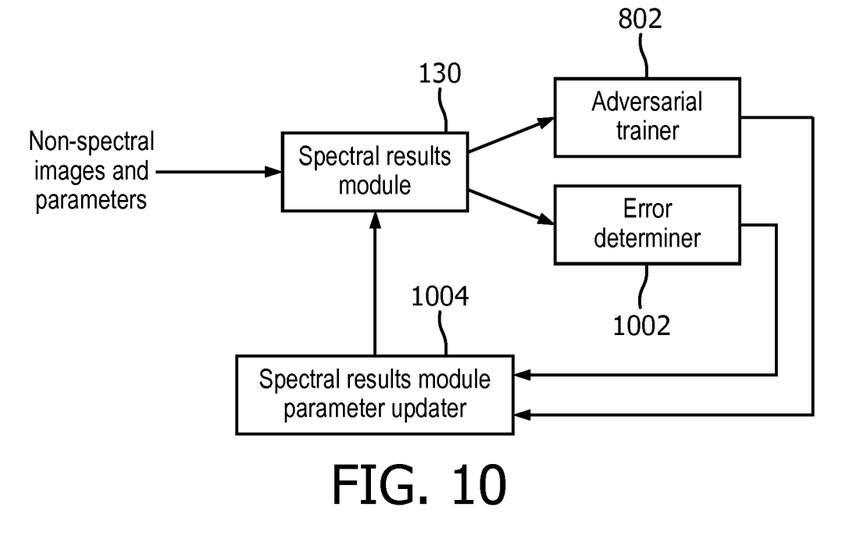
FIG. 10 schematically illustrates training of the spectral basis estimator and/or the spectral image estimator with a hybrid approach that includes the trained adversarial trainer and an error determiner.

FIGS. 8, 9 and 10 illustrate example training of the deep learning algorithm of the spectral results module 130.

Referring first to FIG. 8, an adversarial trainer 802 is trained using a set of initial network parameters. The input includes generated spectral images from a spectral imaging system along with a classification that they are generated spectral images by the spectral imaging system, and estimated spectral images from a non-spectral imaging system along with a classification that they are estimated spectral images from non-spectral image generated by the non-spectral imaging system. The adversarial trainer 802 is trained to distinguish between the generated spectral images generated by the spectral imaging system and the estimated spectral images estimated from non-spectral images generated by the non-spectral imaging system. In one instance, the adversarial trainer 802 is trained as a fully convolutional classification neural network.

Next at FIG. 9, the adversarial trainer 802 is further trained. The input includes a set of generated spectral images from a spectral imaging system and a set of estimated spectral images estimated from non-spectral image generated by a non-spectral imaging system. For this, the classification of the input data sets is known, and the known classification and the classification results of the adversarial trainer 802 are provided to an adversarial parameter updater 902, which updates the network to improve the classification results of the adversarial trainer 802. The adversarial trainer 802 is trained until stopping criteria is met. Examples of stopping criteria include a correct classification percentage, a time duration, a number of update iterations, and/or other stopping criteria. An adversarial network is discussed in Goodfellow, et al., "Generative Adversarial Nets," In: Advances in neural information processing systems, 2672-2680, 10 Jun. 2014.

Next at FIG. 10, the deep learning algorithm of the spectral results module 130 is trained using the trained adversarial trainer 802 and a set of initial network parameters. The input includes a set of non-spectral images from a non-spectral imaging system along with acquisition and reconstruction parameters used to produce the non-spectral images, and a set of non-spectral images from a spectral imaging system produced by combining spectral images along with acquisition and reconstruction parameters used to produce the spectral images and the spectral images. The spectral results module 130 estimates spectral images from the input data sets using its network parameters.

For non-spectral input images from a non-spectral scanner, the estimated spectral images are provided to the trained adversarial trainer 802, which classifies the estimated spectral images as either estimated spectral images from non-spectral image or generated spectral images from a spectral imaging system. Generally, the trained adversarial trainer 802 classifies input without a reference gold truth spectral image data set. For non-spectral input images from a spectral scanner, the estimated spectral images and the generated spectral images are provided to an error determiner 1002, which computes a difference or error between the estimated spectral images and the generated spectral images. In one instance, the difference or error is computed as a root mean square error (RMSE).

A spectral results module parameter updater 1004 receives the classification results from trained adversarial trainer 802 and the error determined from the error determiner 1002. The spectral results module parameter updater 1004 adjusts the network parameters of the spectral results module 130 based on the classification results and error. In one instance, this includes optimizing a loss function that includes at least two terms, one term for the error and another term for the classification. The loss function is optimized to decrease the error between estimated and generated spectral images (e.g., lower the RMSE) and increase the number of classifications of estimated images as generated spectral images due to the estimated images being indistinguishable therefrom.

In one instance, the training described in FIGS. 8-10 is a deep regression neural network hybrid training that includes both 1) ground truth data sets consisting of estimated spectral images estimated from non-spectral images produced by combining generated spectral images generated by a spectral imaging system and the generated spectral images, and 2) data sets without ground truth spectral images, which include estimated spectral images estimated from non-spectral images produced by a non-spectral imaging system.

Training deep regression neural network on ground truth data sets alone to predict spectral images from non-spectral images from a non-spectral imaging system may result in sub-optimal predicted spectral images due to, e.g., variations in image reconstruction pipelines between non-spectral and the spectral imaging system. The approached described herein mitigates this by also including the data sets without the ground truth spectral images in the loss function.

Figure 11:
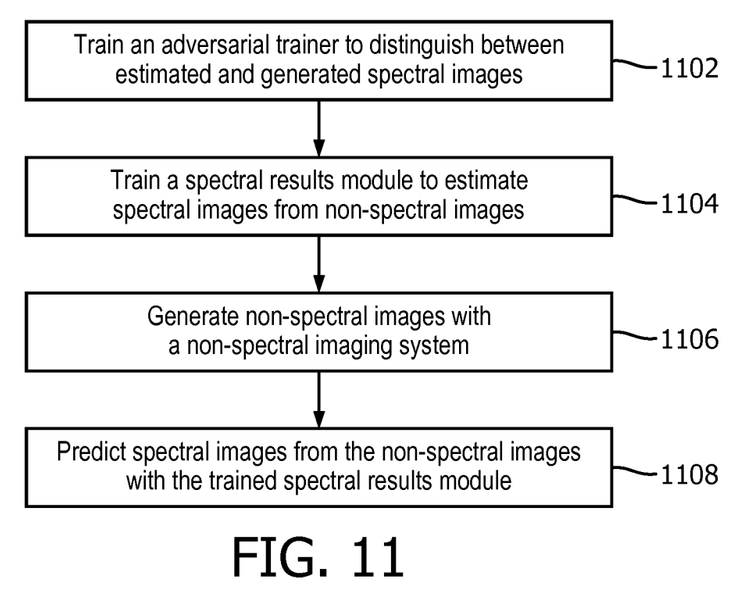
FIG. 11 illustrates an example method in accordance with an embodiment herein.

FIG. 11 illustrates an example method in accordance with an embodiment herein.

At 1102, the adversarial trainer 802 is trained with estimated and generated spectral images to distinguish therebetween, as described herein and/or otherwise.

At 1104, the deep learning algorithm of the spectral results module 130 is trained using the trained adversarial trainer 802 and the error determiner 1002 to estimate spectral images from non-spectral images, as described herein and/or otherwise.

At 1106, non-spectral images are generated with a non-spectral imaging system 102, as described herein and/or otherwise.

At 1108, the trained spectral results module 130 estimates spectral data (basis components and/or images) from the non-spectral images, as described herein and/or otherwise.

Figure 12:
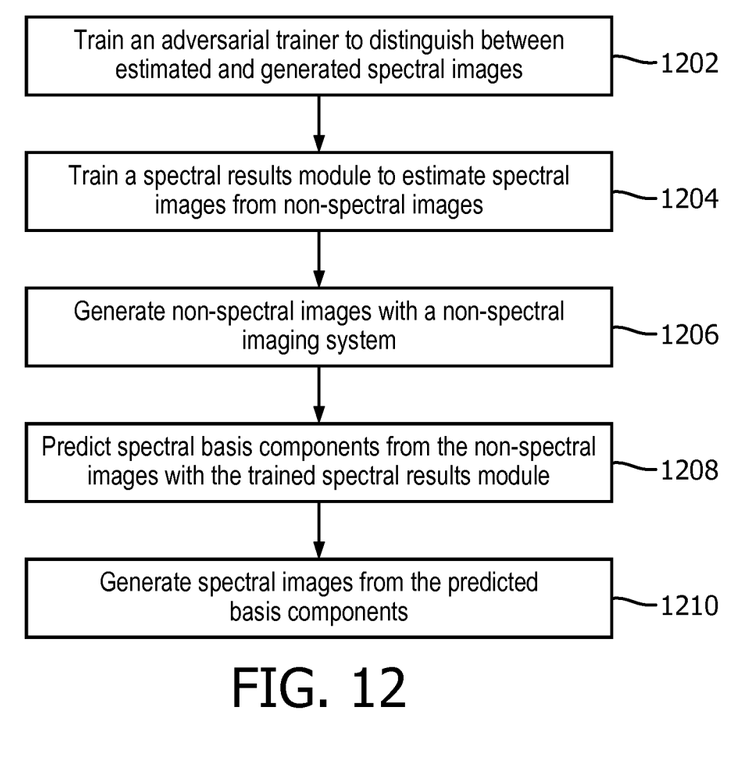
FIG. 12 illustrates another example method in accordance with an embodiment herein.

FIG. 12 illustrates an example method in accordance with an embodiment herein.

At 1202, the adversarial trainer 802 is trained with estimated and generated spectral images to distinguish therebetween, as described herein and/or otherwise.

At 1204, the deep learning algorithm of the spectral results module 130 is trained using the trained adversarial trainer 802 and the error determiner 1002 to estimate spectral images from non-spectral images, as described herein and/or otherwise.

At 1206, non-spectral images are generated with a non-spectral imaging system 102, as described herein and/or otherwise.

At 1208, the trained the spectral results module 130 estimates spectral basis components from the non-spectral images, as described herein and/or otherwise.

At 1210, the trained the spectral results module 130 generates spectral images from the spectral basis components, as described herein and/or otherwise.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium, which is not computer readable storage medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A non-spectral imaging system, comprising:
    a radiation source configured to emit X-ray radiation;
    a detector array configured to detect X-ray radiation and generate a signal indicative thereof;
    a reconstructor configured to reconstruct the signal and generate non-spectral image data; and
    a processor configured to process the non-spectral image data using a deep learning regression algorithm to estimate spectral data from spectral basis components and a spectral image.

2. The system of claim 1, wherein the processor is configured to process the non-spectral image data along with a set of parameters from acquisition parameters employed to acquire the signal and reconstruction parameters employed to reconstruct the signal and generate the non-spectral image to estimate the spectral data.

3. The system of claim 1, wherein the processor is configured to employ a sliding-window deep learning regression algorithm.

4. The system of claim 1, wherein the processor is configured to employ a fully convolution regression network deep learning regression algorithm.

5. The system of claim 1, wherein the processor is configured to estimate the spectral basis components and generate the spectral image from the spectral basis components.

6. The system of claim 1, wherein the processor is configured to estimate the spectral image directly from the non-spectral image data.

7. The system of claim 1, wherein the spectral basis components include a photoelectric effect component and a Compton scattering component, and the spectral image includes at least one spectral image from at least one of an energy band image, a virtual monochromatic image, a contrast agent quantitative image, a virtual non-contrast image, a material cancellation image, an effective atomic number image, and an electron density image.

8. The system of claim 7, wherein the processor is configured to train an adversarial trainer with estimated spectral images from non-spectral images from a non-spectral imaging system and with generated spectral images from a spectral imaging system to distinguish between the estimated spectral images and the generated spectral images.

9. The system of claim 8, wherein the processor is configured to train the deep learning regression algorithm with non-spectral input data using the trained adversarial trainer and a difference determiner, wherein the non-spectral input data includes non-spectral images generated by a non-spectral imaging system and non-spectral images generated by a spectral imaging system.

10. The system of claim 9, wherein the processor is configured to train the deep learning regression algorithm with estimated spectral images generated from the non-spectral images generated by the non-spectral imaging system using the trained adversarial trainer, and with estimated spectral images generated from the non-spectral images produced from spectral images generated by the spectral imaging system based on an error between the estimated spectral images and the spectral images generated by the spectral imaging system.

11. A non-spectral imaging system, comprising:
    a radiation source configured to emit X-ray radiation;
    a detector array configured to detect X-ray radiation and generate a signal indicative thereof;
    a reconstructor configured to reconstruct the signal and generate non-spectral image data; and
    a processor configured to train a deep learning regression algorithm to estimate spectral data from the non-spectral image data using a hybrid training algorithm.

12. The system of claim 11, wherein the processor is configured to train an adversarial trainer with estimated spectral images from non-spectral images from a non-spectral imaging system along with acquisition and reconstruction parameters used to generate the non-spectral images and with generated spectral images from a spectral imaging system along with acquisition and reconstruction parameters used to generate the spectral images to distinguish between the estimated spectral images and the generated spectral images.

13. The system of claim 12, wherein the processor is configured to train the deep learning regression algorithm with non-spectral input data using the trained adversarial trainer and a difference determiner, wherein the non-spectral input data includes non-spectral images generated by a non-spectral imaging system and includes non-spectral images generated by a spectral imaging system.

14. The system of claim 13, wherein the processor is configured to train the deep learning regression algorithm with estimated spectral images generated from the non-spectral images generated by the non-spectral imaging system using the trained adversarial trainer, and with estimated spectral images generated from the non-spectral images produced from spectral images generated by the spectral imaging system based on an error between the estimated spectral images and the spectral images generated by the spectral imaging system.

15. The system of claim 11, wherein the processor is configured to employ a sliding-window deep learning regression algorithm.

16. The system of claim 11, wherein the processor is configured to employ a fully convolution regression network deep learning regression algorithm.

17. The system of claim 11, wherein the processor is configured to estimate the spectral basis components and generate the spectral image from the spectral basis components.

18. The system of claim 11, wherein the processor is configured to directly estimate the spectral image from the non-spectral image data.

19. A non-transient computer readable storage medium encoded with computer readable instructions, which, when executed by a processor of a computing system, causes the processor to:

emit X-ray radiation with a radiation source;
detect emitted X-ray radiation with a detector array and generate a signal indicative thereof;
reconstruct the signal and generate non-spectral image data; and
process the non-spectral image data using a trained deep learning regression algorithm to estimate spectral data from a group consisting of spectral basis components and a spectral image.

20. The non-transient computer readable storage medium of claim 19, wherein executing the computer readable instructions further causes the processor to train the deep learning regression algorithm using a deep spectral hybrid training procedure.

* * * * *